United States Patent

Hutcheon et al.

[11] Patent Number: 5,807,295
[45] Date of Patent: Sep. 15, 1998

[54] MEDICAL ARTICLES

[75] Inventors: Steven David Hutcheon, St. Mary's; William Pigg, Elvington, both of United Kingdom

[73] Assignee: Smith & Nephew plc, London, United Kingdom

[21] Appl. No.: 716,305
[22] PCT Filed: Mar. 30, 1995
[86] PCT No.: PCT/GB95/00758
  § 371 Date: Sep. 27, 1996
  § 102(e) Date: Sep. 27, 1996
[87] PCT Pub. No.: WO95/26698
  PCT Pub. Date: Oct. 12, 1995

[30] Foreign Application Priority Data

Mar. 30, 1994 [GB] United Kingdom .................. 9406273
May 25, 1994 [GB] United Kingdom .................. 9410510

[51] Int. Cl.$^6$ ........................................ A61F 5/00
[52] U.S. Cl. .................... 602/42; 602/6; 602/8; 66/87
[58] Field of Search .............. 602/41–63, 6–10; 128/888, 889; 66/87

[56] References Cited

U.S. PATENT DOCUMENTS 4,753,232  6/1988  Ward ........................................ 602/52
5,385,036  1/1995  Spillane et al. ......................... 66/87

FOREIGN PATENT DOCUMENTS 531096  3/1996  European Pat. Off. .

*Primary Examiner*—Richard J. Apley
*Assistant Examiner*—Kim Lee
*Attorney, Agent, or Firm*—Larson & Taylor

[57] ABSTRACT

A medical bandaging material, for example, for use as a wound dressing, soft-tissue support bandage, brace or orthopaedic splinting bandage, comprises two superposed layers of, for example, a woven, knitted or non-woven material spaced apart by strands of mono-filamentary or fibrous layers. The interstitial spaces may be filled with a hardenable resin and/or pharmacologically active agent.

22 Claims, 2 Drawing Sheets

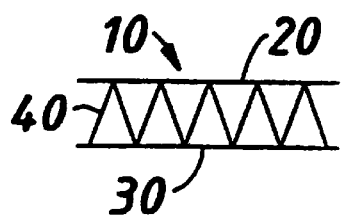
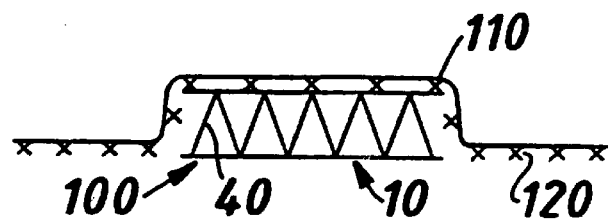
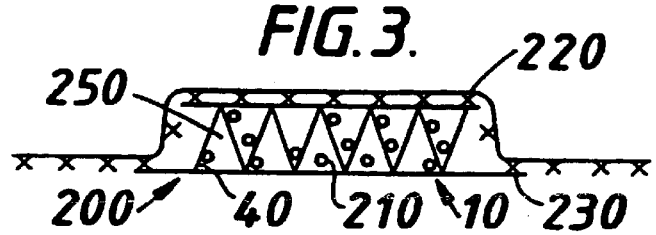
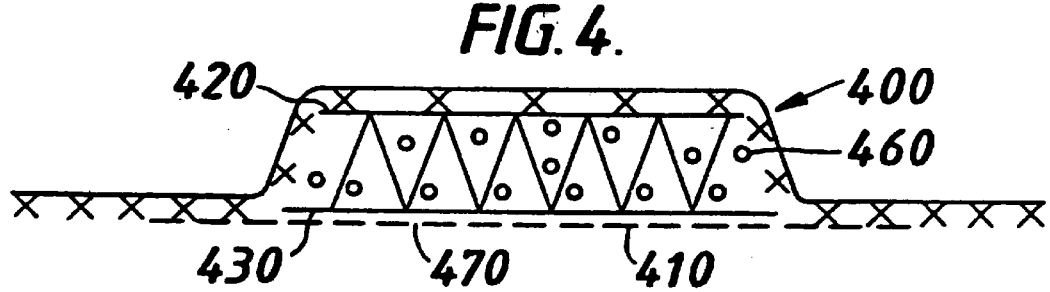
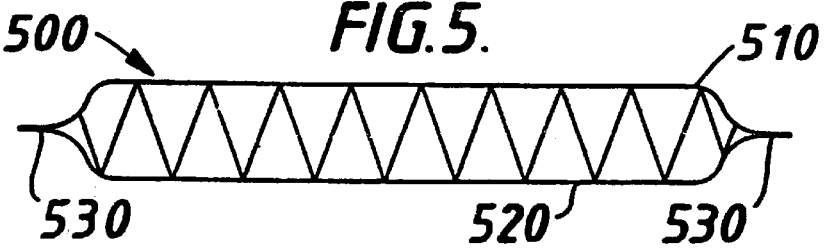
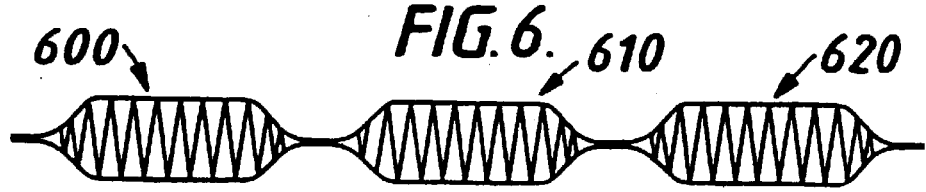

MEDICAL ARTICLES

FIELD OF THE INVENTION

The present invention relates medical articles comprising fabrics having spaced apart layers.

Medical articles comprising several layers are well known in the art. EP-A-0 071 211 discloses a medical article comprising two outer layers and an intermediate layer wherein the intermediate layer contains mineral particles. The layers are sewn together thereby trapping the mineral particles.

SUMMARY OF THE INVENTION

According to the present invention there is provided a medical bandaging material comprising a first body facing layer and a second layer superposed over said first layer in a spaced apart relationship wherein a plurality of strands extend between the first and second layers thereby to maintain them in said spaced apart relationship. Preferably the filaments are resilient thereby allowing the bandage to be resiliently deformable.

As used herein the term 'strands' includes mono-filamentary strands or multi-filamentary structures such as fibers. The strands may be in the form of yarns.

BRIEF DESCRIPTION OF THE DRAWINGS

FIG. 1 is a schematic cross sectional view of one embodiment of a bandage according to the present invention.

FIG. 2 is a schematic cross sectional view of one embodiment of a bandage according to the present invention.

FIG. 3 is a schematic cross sectional view of one embodiment of a bandage according to the present invention.

FIG. 4 is a schematic cross sectional view of one embodiment of a bandage according to the present invention.

FIG. 5 is a schematic cross sectional view of one embodiment of a bandage according to the present invention.

FIG. 6 is a schematic cross sectional view of one embodiment of a bandage according to the present invention.

DESCRIPTION OF PREFERRED EMBODIMENTS

Figure 7:
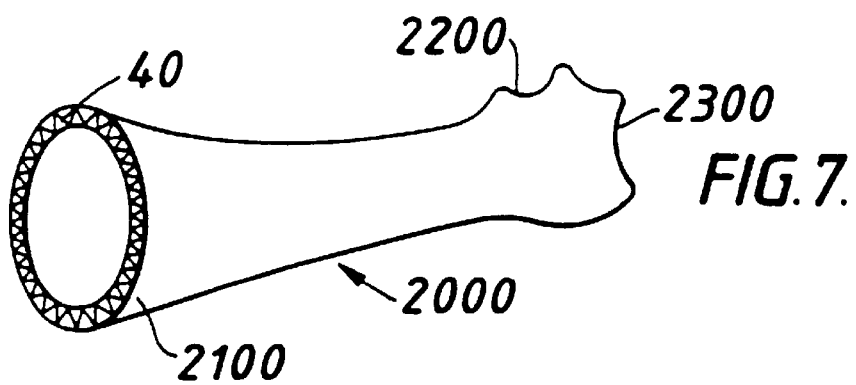
FIG. 7 is a schematic representation illustrating the use of the bandage according to the present invention.

In one embodiment of the invention the bandage is a medical dressing used for covering wounds such as lesions, burns, donor sites and surgical incisions.

In an alternative embodiment of the present invention the bandage is a medical support product.

The term "medical support product" is used herein to include products for medical use which are designed to at least partially support or immobilize a body member or part thereof. Medical support products include braces, splints, casts, bandages, collars, upper body supports, lower body supports, joint supports, orthopaedic padding (e.g. for reducing the risk of strain for key-board users), or long term support cushioning for this in need of upper or lower limb support etc.

If hydrophobic fibers (e.g. polypropylene) are used as the strand material, the bandage invention can be used as undercast padding and, if a suitably apertured structure is used, may provide the undercast padding with a 'quick drain' ability allowing the wearer to immerse a supported limb under water (e.g. when bathing). When the limb is removed from water the cast can dry out quickly due to the efficient draining provided by the undercast padding.

Preferably the spacing between the first and second surfaces is at least 0.5 mm. This may be across all or a substantial portion of the bandage e.g. across at least 50%, of the volume thereof. The spacing may be as large as desired for the particular use for which the dressing is intended but is typically no more than 5 cm (across all or a substantial portion of the bandage).

One or both layers may be substantially planar. The layers may be substantially parallel to one another over all or over a substantial part of the bandage. In many embodiments however it may be desirable particularly at edge regions of the fabric that the one or both layers are inclined to each other.

Thus, the fabric may have one or more tapered edges. The edges may be held together by stitching, welding or adhesive for example.

The first and second opposing surfaces of the layers may be present as surfaces of first and second opposing sheets of knitted, woven or non-woven material. The sheets may be formed of the same or different material.

Preferably however both the first and second sheets are knitted. Any desirable knit may be used for forming the first and second sheets, for example warp knit, weft knit, and may also be patterned (e.g. with a waffle pattern).

Most preferably warp knitting (e.g. using Raschel warp knitting machinery) is used.

The strands may be formed from one or more fibers which interconnect the first and second sheets. They may be secured to the first and second opposing sheets by any appropriate means e.g. by knitting, weaving, the use of adhesives or welding (which is particularly apt for thermoplastic materials). Desirably knitting is used.

Thus, in a most preferred embodiment, the bandage comprises knitted first and second spaced sheets and a plurality of strands which interconnect the first and second opposing surfaces.

Desirably the bandage is formed as a unit in a single process. The bandages of the invention may be produced by a process similar to that disclosed in U.S. Pat. No. 4601940 (Fischer). The fabric can be made by using a warp or tricot or Raschel knitting machine having at least three guide bars and two rows of spaced needles. Two of the guide bars feed thread which is knitted to form two sheets which are held spaced apart from one another. Simultaneously with forming the two sheets, strands, (which in U.S. Pat. No. 4601940 are referred to as filler threads), are used to interconnect the two sheets by knitting. The filler threads are produced from a fiber fed through a third guide bar which is located between the two guide bars feeding the thread to form the knitted sheets.

Another apt process for forming a bandage is disclosed in E-PA-0529671, in which a Raschel warp knitting machine with two needle bars and six thread guide bars are used to form a fabric which is said to provide a cushion, suitable for use in car seat upholstery. The knitted fabric may comprise opposed sheets formed using the same or a different knitting construction. Both may have two threads on the front and back needle bars. The strands (referred to in EP-A-0529671 as "pile") may also have two thread guides, but alternatively may have only one. Cord, tricot, atlas or satin tricot lapping may be used.

The strands should be sufficiently resilient to maintain the first and second opposed sheets in spaced relation to one another when pressure is not applied to the bandage. Thus the bandage should be self-supporting.

Preferably the strands are arranged so as to prevent the opposed sheets contacting one another when a compressive force of up to 0.5 N/m$^2$ more preferably of up to 2.5 N/m$^2$ is applied to the fabric in a direction opposing the force exerted by the spacer elements to keep the opposed sheets apart.

It is also preferred however that the strands are capable of deforming (e.g. bending) so as to provide a cushioning effect. Thus the strands are desirably formed of resiliently deformable material.

By varying the material, diameter, length and/or the number of strands per unit volume the characteristics of the bandage (resilience, compressibility, etc.) can be tailored for different applications.

Different strands may be used within the same bandage.

Apt strands may be formed from polyester, polyamide (e.g. Nylon™), polypropylene, polyethylene, cotton or other fibrous materials. Elastomeric materials may also be used (e.g. Lycra™, Spandex™ or elastomeric polyurethanes) and may be incorporated together with non-elastomeric strands.

Permeable/hollow fibers may also be used such as Celgard (Trade Mark) available from Hoescht-Celanese.

Alginate comprising strands may be used and are advantageous in that they are absorbent. They are obtainable from Courtaulds. Superabsorbent fibers such as Oasis (Trade Mark) from technical absorbents may also be used.

Strands may also be used which comprise chitosan. These are advantageous in that they are absorbent and may also actively promote wound healing by peroxide emission. Chitosan comprising fibers are obtainable from Novasso 07, Finland.

By using strands, bandages can be provided with a substantial void volume which can then be filled with any desired filler material which may be advantageous in wound care. Typically the void volume comprises at least 50%, advantageously at least 80% of the total volume between the opposing sheets. Thus pharmaceutically active agents may be provided (e.g. antimicrobial agents, such as chlorhexidine) and may be used together with pharmaceutically acceptable carrier materials. Chitosan or alginates may also be used as a filler material.

Other possible filler materials include odor absorbing materials (e.g. activated charcoal) and absorbent materials (e.g. superabsorbents.

Any appropriate means may be used to incorporate the aforesaid materials. For example, a gel may be formed in situ in the bandage by introducing the precursor(s) to the gel into the fabric and allowing curing of the gel to occur in situ. The precursor(s) may be introduced by injection, by the use of pressure rollers (e.g. to force material into the bandage) or simply by allowing the bandage to absorb the precursor (s), (e.g. in a dipping process).

The gel may incorporate one or more of the aforesaid filler materials. Apt gels for use in the present invention are:— carboxy methyl cellulose based gels such as IntraSite* Gel, Alginate Gels, Chitosan Gels, silicon gels such as Cicacare* Gel (*Trade Marks of products obtainable from Smith & Nephew Plc, Hull, U.K.). Suitable Hydrogels are disclosed in EP-A-0100458. These gels may be formed by hydrating a gel precursor material and adding filler material (if desired) prior to introducing the gel and filler material to the bandage. Alternatively (as indicated above) the gel may be formed in situ.

Other means for incorporating filler materials include forcing the materials into the bandage by blowing or by the use of suction, as is frequently used for forming air laid textile materials.

The bandage may be used in any suitable type of medical dressing or support applications. The bandage can be provided with an attachment means for attaching to a patient. For example, the bandage may be provided with an adhesive coating, with one or more ties, or with a hook and eye fastener system (e.g."Velcro"™ material) so that the bandage can be releasably attached to a body member. If the fabric is surface roughened this can provide a surface to which hooks (e.g. of a "velcro" system) can be releasably attached without the need for providing separate eyes.

Alternatively the bandage may have tubular configuration so that it can be slid over a body member. The product may have a region shaped complimentarily to a body surface it is to be placed against and may define one or more apertures through which body members e.g. fingers and toes can be inserted.

The bandage (together with any fastening means used) may provide the sole support required and this type of arrangement may be used in tubular bandages for example.

Alternatively, the bandage may be used in conjunction with a rigid component (e.g. a metal or plastics component) and this can advantageously be used in splints or braces for example. Here the bandage can be placed between the rigid component and a body surface so as to provide a cushioning effect. It may be secured to the rigid component e.g. by adhesive or lamination, but this is not essential since strapping for example can be used to maintain the bandage and the rigid component as desired relative to one another.

The bandage may also be used in combination with elastomeric support materials such as neoprene. Elastomeric materials are commonly used in the treatment of strains and sprains, particularly those occurring at joints. Such materials have low moisture permeability and hence may be uncomfortable to wear.

The use of a bandage as an inner layer of a support product comprising an elastomeric support material may provide an air cushion and permit transport of moisture away from skin. The bandage can be incorporated in a support product comprising an elastomeric support material as a continuous lamination. Alternatively, sections of the bandage can be laminated to the inner surface of the elastomeric material to provide cushioning at specific places. The bandage can be elastic or inelastic.

The bandage product may be impregnated with a curable or hardenable material so that it can form a cast or splint. For example a moisture curable resin which by immersion in water may be included. For example, isocyanate or siloxane based resins may be used. A low temperature thermoplastic resin (e.g. polycapralactone) may also be used. This can be activated by heat and then the support product can be moulded to shape. Other resin systems e.g. light activated vinyl ether systems can be used.

The curable material may advantageously be incorporated between the first and second spaced apart surfaces of the bandage. Thus a large amount of resin can be loaded into the bandage. Alternatively impregnation of the fabric forming the surfaces may be carried off to give a high rigidity/weight ratio.

The bandage containing curable or hardenable resin may be used as a tubular or strip casting bandage. Alternatively, it may be used as a splint (e.g. a slab splint), which can then be held in place by any desirable securing means.

The bandage may be used in any suitable type of medical support product.

A backing sheet overlying the bandage may be provided, for example, to protect the bandage from the external environment when a dressing comprising a bandage is applied to a patient. The backing sheet is preferably formed of a material which is impermeable to liquid water but which is permeable to moisture vapour.

The backing sheet may be coated with an adhesive, which may be a pressure sensitive adhesive. The adhesive may be discontinuous or continuous. Suitable adhesive coated backing sheets which are impermeable to liquid water but permeable to moisture vapour are described in UK Patent Specification No. 1280631.

Apt pressure sensitive adhesive coated moisture vapor permeable, liquid water impermeable materials suitable for forming a backing sheet are also disclosed in WO88/01877.

Preferably the combination of backing layer and adhesive has a moisture vapour transmission rate (MVTR) of above 800 g/m$^2$/24 h e.g. of more than 1200 g/m$^2$/24 h, e.g. from 1400 to 2000 g/m$^2$/24 h.

The MVTR values referred to above are as measured by the Payne Permeability Cup Method referred to in WO88/01877 at 100% to 10% relative humidity difference and at 37° C., when the adhesive is in contact with moisture vapour.

It may be desirable to provide a net adjacent one of the layers of the bandage so as in the case of the body facing layer, to reduce the likelihood of material from the bandage entering a wound and/or to aid in holding the bandage in place. The net may be elastomeric and may be adhesive coated.

The bandages of the present invention may be used in pressure relieving dressings. These are dressings which are used to treat wounds where it is particularly important that the wounds are not subject to high pressures. This is true in the treatment of bed sores or skin ulcers, which can be very painful when placed under pressure. Pressure relieving dressings may also be used where there is no wound but relief of pressure is still desired (e.g. as a prophylactic measure).

Bandages can function to absorb much of the pressure which might otherwise be applied to a wound when a patient lies down or subjects the wound to accidental impacts. By varying the length, number, type and/or width of the strands used, bandages can be tailored to absorb pressure to a desired degree.

Indeed the bandages are useful in all dressings where absorbency and/or resilient deformability is desired. They are also useful for providing spaces in which filler materials can be placed, such filler materials may advantageously be provided as active ingredients in controlled release form so as to act upon a wound site over a period of time of e.g. several hours, days or weeks.

Bandages of the present invention may advantageously be provided in sealed packages which are desirably sterile. Bandages of the present invention may be provided with one or more release sheets (e.g. silicon coated release paper) to give a removable cover for adhesive which is to be used in applying the dressing to a patient's skin.

When used as a medical support product bandages of the invention can function to absorb much of the pressure which might otherwise be applied to a body surface when a patient lies down or is subject to accidental impacts. By varying the length, number, type and/or width of the strands used, bandages can be tailored to absorb pressure to a desired degree.

They are advantageous over foam and other materials which have conventionally been used in medical support products since they can provide a high degree of support to a patient. Furthermore, relatively small thickness of material can be used whilst still providing a high degree of support to a patient. The patient comfort an be significantly enhanced.

BRIEF DESCRIPTION OF THE DRAWINGS

Figure 8:
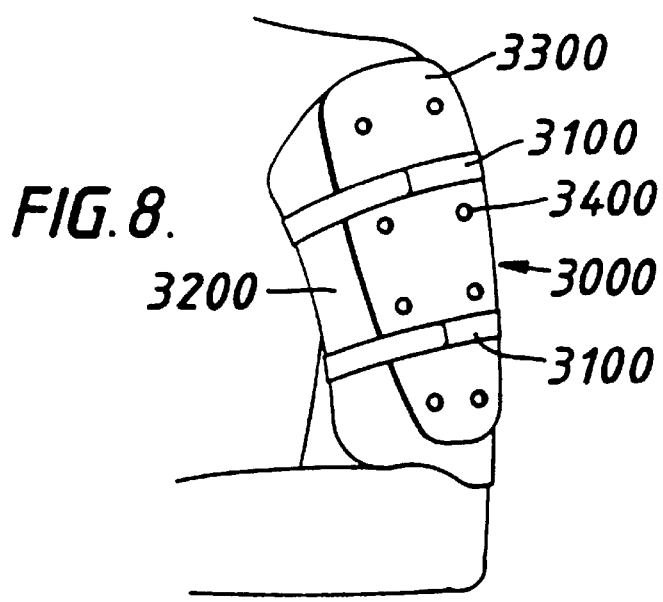
FIG. 8 is a schematic representation illustrating the use of the bandage according to the present invention.

The present invention will now be described by way of example only with reference to the accompanying drawings in which FIGS. 1 to 6 are schematic cross-sectional views of various embodiments of bandages according to the present invention, and FIGS. 7 and 8 are schematic representations illustrating the use of bandages of the present invention as splinting materials.

Figure 9A:
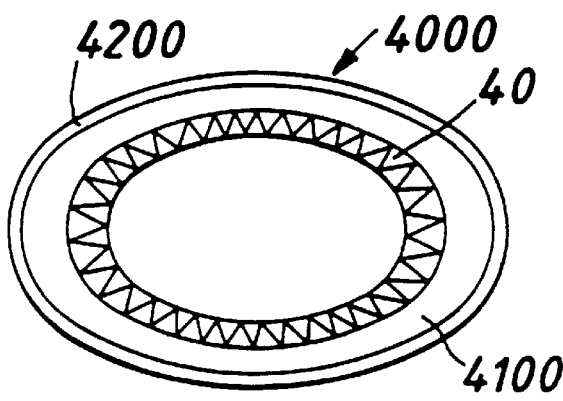
FIGS. 9a and 9b show longitudinal sections through a support product comprising an elastomeric material and bandage.

FIGS. 9a and b show longitudinal sections through a support product comprising an elastomeric material and bandage.

Referring now to FIG. 1, the bandage shown schematically is a composite 10 which comprises upper and lower opposed sheets 20 and 30 which are interconnected by fibrous spacer members or strands 40. The upper and lower opposed sheets 20, 30 are substantially planar and are arranged in substantial parallel relation to one another.

The fabric is formed by using double face Raschel knitting machines (double needle bar Raschels with six thread guide bars).

There are approximately 120 strands per square centimetre of fabric (taken as a section at right angles to the planes of sheets 20 and 30) and the fibres have an average diameter of approximately 0.20 mm.

Referring now to FIG. 2, medical dressing 100 is shown in schematic longitudinal section. Medical dressing 100 comprises a moisture vapour permeable backing layer 110 which is coated with an adhesive 120 and composite 10. Backing layer 110 which acts as a barrier to the passage of liquid water or bacteria across it, but allows moisture vapour (e.g. from sweat or wound exudate) to pass across it. The film is thus breathable.

The adhesive coated moisture vapour permeable layer is used to hold composite 10 in place against the skin of a patient. The bandage facilitates evaporation of moisture from, for example, a wound site by providing a substantial space within the dressing in which moisture vapour can be present, before passing across the moisture vapour permeable film. The material of which the composite 10 is formed functions to absorb exudate from a wound site and can thus also aid in reducing maceration which might otherwise occur due to prolonged exposure of skin to moisture. Furthermore, under conditions of high exudation from a wound, the strands 40 can aid in channelling liquid away from a wound site by capillary action.

Referring now to FIG. 3, a dressing 200 is shown comprising a composite 10 into which activated carbon particles 210 have been incorporated. The carbon particles are obtainable from BDH of Lufterworth, Leicestershire as activated charcoal. These particles 210 are incorporated by spraying the particles into the space 250 between upper and lower opposing sheets (220 and 230).

The particles 210 function to reduce by absorption the level of undesirable odours which might otherwise emanate from infected wounds to the environment external to dressing 200.

Turning now to FIG. 4, an alternative dressing 400 is shown from that illustrated in FIG. 3, wherein a wound contact layer 410 of perforated ethylene-vinyl acetate copolymers (EVA)/high impact polystyrene (HIP) blend film is located underneath the bandage. In this embodiment there is no need for the lower sheet 430 of the bandage to be larger than the upper sheet 420 since the perforated film 410 provides a cover which prevents activated carbon particles 460 entering a wound since the perforations are small relative to the particles. The perforations 470 in the EVA-HIPS film enhance the breathability of the dressing and can allow wound exudate to pass across the film. This is useful if an absorbent material is located within the bandage to absorb wound exudate.

If desired the lower sheet 230 shown in FIG. 3 may be similarly perforated.

In some applications it may be desirable to replace the perforate film with a layer which is impermeable to liquid wound exudate but which allows moisture vapour to pass across it (e.g. a moisture vapour film).

FIG. 5 illustrates how a sealed compartment 500 can be formed using a bandage. This is achieved by forming a continuous seal 530 around the periphery of the fabric between upper and lower sheets 510, 520. The sealing may be achieved by any appropriate method (e.g. heat sealing, edge-stitching, taping, clamping etc.).

In FIG. 6 several sealed compartments 600, 610, 620 are shown. There may be a large number of these compartments which may have edges in the form of regular polygons to achieve a high efficiency of packing of compartments side by side (e.g. in a honeycomb arrangement). Different compartments may contain different materials e.g. different absorbents and/or different pharmaceutically active agents (which may be in controlled release form).

The compartment 500 shown in FIG. 5 and the compartments 600, 610, 620 shown in FIG. 6 may be used in wound dressings as desired. They may be partially or totally covered with backing material and may be provided with adhesive. They may simply be used as pads, which can be secured to a patient by any appropriate securing means (e.g. adhesive tape or bandaging).

Turning now to FIG. 7, a tubular bandage 2000 is shown which is formed from the composite 10 illustrated in FIG. 1. Fibrous spacer members 40 can be seen at end 2100 of the bandage and ensure that the tubular bandage provides good support for the forearm of a patient. Apertures 2200 and 2300 are for the thumb and the fingers of a patient respectively. In order to allow the bandage 2000 to be easily slid over a patient's forearm, it is elastically deformable, being at least partially knitted from Lycra (Trade Mark) thread. This also facilitates a good fit of the bandage 2000.

FIG. 8 shows a splinting assembly 3000 which is held in position by hook and eye fasteners 3100. The inner layer of the assembly 3000 comprises a bandage 3200, which is wrapped around a patient's upper arm until a desired degree of cushioning is attained. A rigid splint member 3300 formed of a hard plastics material is then placed around that part of the forearm for which splinting is desired so that it lies over the bandage 3200. To assist breathability it is provided with apertures, 3400. Fastening can then be achieved as aforesaid.

Figure 9B:
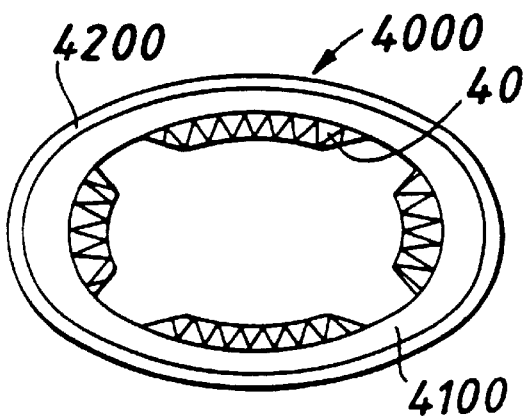

FIG. 9a and b illustrate a bandage 40 incorporated into a support product 4000 comprising an elastomeric layer of neoprene and an outer fabric layer. FIG. 9a shows a continuous layer bandage laminated to the neoprene layer whereas, in FIG. 9b sections of bandage are laminated to the inside of the neoprene surface.

In use the bandage serves to provide cushioning and to allow moisture vapour to be transported away from the skin of the wearer.

I claim:

1. A medical bandaging material comprising a first, body facing layer, and a second layer superposed over said first layer in a spaced apart relationship wherein a plurality of strands extend between the first and second layers, wherein said strands maintain said first and second layers in spaced apart relationship such that a space is present between the first and second layers, said strands being resiliently deformable and interconnected into the first and second layers, and wherein a hardenable resin or a pharmacologically active material is contained within the space between the first and second layers.

2. A material as claimed in claim 1 wherein the first and second layers are spaced apart by at least 0.5 mm.

3. A material as claimed in claim 1 wherein said first and second layers are immediately adjacent each other over part of the material.

4. A material as claimed in claim 3 wherein said first and second layers are immediately adjacent each other along at least one peripheral edge of at least one of the said layers.

5. A material as claimed in claim 1 wherein at least one of said first and second layers comprises a sheet of a knitted, woven, or non-woven material.

6. A material as claimed in claim 1 wherein the strands comprise a fibrous material.

7. A material as claimed in claim 1 wherein the strands are knitted into the first and second layers.

8. A material as claimed in claim 1 wherein at least one of said first or second layers or strands is comprised of a thermoplastic material.

9. A material as claimed in claim 1 wherein the materials comprising the first and second layers are flexible.

10. A material as claimed in claim 1 wherein a third layer of material overlies said second layer.

11. A material as claimed in claim 10 wherein said third layer is moisture vapor permeable.

12. A material as claimed in claim 10 wherein said third layer extends beyond the area of the second layer.

13. A material as claimed in claim 1 wherein said third layer comprises means for attachment to a body.

14. A material as claimed in claim 13 wherein said attachment means comprises an adhesive layer.

15. A material as claimed in claim 1 wherein a further layer underlies said first layer.

16. A material as claimed in claim 15 wherein said further layer comprises a net.

17. A material as claimed in claim 1 wherein said hardenable resin comprises a water-hardenable polyisocyanate functional resin, a water hardenable siloxane functional resin, a light activated vinyl ether resin or a thermoplastic resin.

18. A material as claimed in claim 1 wherein a pharmacologically active agent in controlled release form is contained in said space.

19. A wound dressing comprising a bandaging material as claimed in claim 1.

20. A soft tissue support bandage comprising a bandaging material as claimed in claim 1.

21. An orthopaedic splinting bandage comprising a bandaging material as claimed in claim 1.

22. An orthopaedic brace comprising a bandaging material as claimed in claim 1.

* * * * *